(12) United States Patent
Walker et al.

(10) Patent No.: US 6,253,098 B1
(45) Date of Patent: Jun. 26, 2001

(54) DISPOSABLE PULSE OXIMETER ASSEMBLY AND PROTECTIVE COVER THEREFOR

(75) Inventors: Steven C. Walker, Olmos Park; John M. Shepherd, Fort San Antonio, both of TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/389,353

(22) Filed: Sep. 3, 1999

Related U.S. Application Data

(60) Provisional application No. 60/099,579, filed on Sep. 9, 1998, and provisional application No. 60/101,079, filed on Sep. 18, 1998.

(51) Int. Cl.[7] .................................................. A61B 5/00

(52) U.S. Cl. ...................... 600/344; 600/310; 600/340

(58) Field of Search .................................... 600/310, 322, 600/323, 340, 344, 324, 325, 326, 327, 328, 331, 332, 334, 337, 339, 341, 549; 356/41; 433/116

(56) References Cited

U.S. PATENT DOCUMENTS

| | | |
|---|---|---|
| 3,908,665 | 9/1975 | Moses . |
| 4,222,391 * | 9/1980 | Rawson et al. ........................ 600/549 |
| 4,270,531 | 6/1981 | Blachly . |
| 4,495,945 | 1/1985 | Liegner . |
| 4,586,513 | 5/1986 | Hamaguri . |
| 4,621,643 | 11/1986 | New, Jr. et al. . |
| 4,624,572 | 11/1986 | Van Den Bosch . |
| 4,651,746 | 3/1987 | Wall . |
| 4,676,240 | 6/1987 | Gardy . |
| 4,700,708 | 10/1987 | New, Jr. et al. . |
| 4,796,636 | 1/1989 | Branstetter et al. . |
| 4,830,014 | 5/1989 | Goodman et al. . |

(List continued on next page.)

FOREIGN PATENT DOCUMENTS

| | | |
|---|---|---|
| 4 42 260 A1 | 5/1996 | (DE) . |
| WO 86/00207 | 1/1986 | (WO) . |
| WO 90/01293 | 2/1990 | (WO) . |
| WO 90/07907 | 7/1990 | (WO) . |
| WO 6/29927 | 10/1996 | (WO) . |
| WO 96/31155 | 10/1996 | (WO) . |
| WO 97/42903 | 11/1997 | (WO) . |

OTHER PUBLICATIONS

Sheridan et al., "Intraoperative Reflectance Oximetry in Burn Patients," Journal of Clinical Monitoring, Jan. 1995, vol. 11 (1): 32–34.

Faisst et al., "Intrapartum Reflectance Pulse Oximetry: Effects of Sensor Location and Fixation Duration on Oxygen Saturation Readings," Journal of Clinical Monitoring, Sep. 1997, vol. 13 (5): 299–302.

Izumi et al., "Accuracy and Utility of a New Reflectance Pulse Oximeter for Fetal Monitoring During Labor," Journal of Clinical Monitoring, Mar. 1997, vol. 13 (2): 103–108.

(List continued on next page.)

*Primary Examiner*—Eric F. Winakur
(74) *Attorney, Agent, or Firm*—Elizabeth Arwine; Charles H. Harris

(57) ABSTRACT

This invention is a protective covering to protect off-the-shelf disposable pulse oximeter sensors from bodily or surgical fluids. The protective covering will envelop and encase the inserted pulse oximeter sensor up to a point on the connection cable extending from the pulse oximeter sensor. The protective covering is a polypropylene, rubber, or similar material, which preferably is tapered from the large width at the entrance to the narrower width at the blind end. The protective covering is bilaminar in nature to contain a substantially rectangular pulse oximeter.

19 Claims, 2 Drawing Sheets

U.S. PATENT DOCUMENTS

| | | |
|---|---|---|
| 4,854,699 | 8/1989 | Edgar, Jr. . |
| 4,859,057 | 8/1989 | Taylor et al. . |
| 4,865,038 * | 9/1989 | Rich et al. ............................ 600/344 |
| 4,867,557 | 9/1989 | Takatani et al. . |
| 4,880,304 | 11/1989 | Jaeb et al. . |
| 4,890,619 | 1/1990 | Hatschek . |
| 5,040,539 | 8/1991 | Schmitt et al. . |
| 5,069,214 | 12/1991 | Samaras et al. . |
| 5,090,410 * | 2/1992 | Saper et al. ............................ 602/41 |
| 5,193,544 | 3/1993 | Jaffe . |
| 5,197,875 * | 3/1993 | Nerli ...................................... 433/80 |
| 5,203,329 | 4/1993 | Buchanan . |
| 5,217,012 | 6/1993 | Young et al. . |
| 5,226,417 * | 7/1993 | Swedlow ............................. 600/322 |
| 5,246,003 | 9/1993 | Delonzor . |
| 5,282,464 | 2/1994 | Brain . |
| 5,329,922 | 7/1994 | Atlee, III . |
| 5,337,744 * | 8/1994 | Branigan ............................. 600/407 |
| 5,355,874 | 10/1994 | Bertram . |
| 5,357,954 | 10/1994 | Shigezawa et al. . |
| 5,361,757 | 11/1994 | Smith et al. . |
| 5,413,101 | 5/1995 | Sugiura . |
| 5,417,207 | 5/1995 | Young et al. . |
| 5,494,032 | 2/1996 | Robinson et al. . |
| 5,595,176 | 1/1997 | Yamaura . |
| 5,596,986 | 1/1997 | Goldfarb . |
| 5,619,992 * | 4/1997 | Guthrie et al. ....................... 600/310 |
| 5,638,593 * | 6/1997 | Gerhardt ............................. 29/592.1 |
| 5,673,693 | 10/1997 | Solenberger . |
| 5,678,544 | 10/1997 | Delonzor et al. . |
| 5,715,816 | 2/1998 | Mainiero et al. . |
| 5,743,261 | 4/1998 | Mainiero et al. . |
| 5,755,226 | 5/1998 | Carim et al. . |
| 5,797,841 | 8/1998 | Delonzor et al. . |
| 5,800,349 | 9/1998 | Isaacson et al. . |
| 5,817,009 | 10/1998 | Rosenheimer et al. . |
| 5,839,439 | 11/1998 | Nierlich et al. . |
| 5,954,050 | 9/1999 | Christopher . |
| 5,983,120 | 11/1999 | Groner et al. . |
| 5,991,648 | 11/1999 | Levin . |

OTHER PUBLICATIONS

Hayes, et al., "Quantitative Investigation of Artefact in Photoplethysmography and Pulse Oximetry for Respiratory Exercise Testing," Aug. 27, 1998, Web Article: http://www.lut.ac.uk/departments/el/research/optics/ppgraphy/paper2c.htm.

Anonymous, "Photon Flow For Pulse Oximetry," Sep. 15, 1995, Web Article: http://www.llnl.gov/bbrp/healthcare/projects/pfpulseoxim.html.

Heathgate Data Corp., "Pulse Oximetry," Jun. 13, 1997, Web Article: http://www.healthgate.com/healthgate/free/dph/static/dph.0200.shtml.

Jobes, et al., "Monitoring of Arterial Hemoglobin Oxygen Saturation Using a Tongue Sensor," Anesthesia & Analgesia, Feb., 1988, vol. 67, pp. 186–188.

O'Leary, et al., "Buccal Pulse Oximeter Is More Accurate Than Finger Pulse Oximeter in Measuring Oxygen Saturation," Anesthesia & Analgesia, Oct., 1992, vol. 75, pp. 495–498.

Cote, et al., "Tongue Oximetry in Children with Extensive Thermal Injury: Comparison with Peripheral Oximetry," Can. Journal Anaesth., May, 1992, vol. 39, Issue 5, pp. 454–457.

Reynolds, et al., "Influence of Sensor Site Location on Pulse Oximetry Kinetics in Children," Anesthesia & Analgesia, 1993, vol. 76, pp. 751–754.

Faisst, et al., "Reflectance Pulse Oximetry in Neonates," European Journal of Obstetrics & Gynecology and Reproductive Biology, Aug., 1995, vol. 61, pp. 117–122.

* cited by examiner

DISPOSABLE PULSE OXIMETER ASSEMBLY AND PROTECTIVE COVER THEREFOR

This application claims priority from U.S. provisional Application Ser. No. 60/099,579, filed Sep. 9, 1998 and U.S. provisional Application Ser. No. 60/101,079, filed Sep. 18, 1998.

I. FIELD OF THE INVENTION

The invention is directed to a method and device for measuring blood oxygenation in areas where bodily fluids may compromise electrical components. More particularly, the invention relates to a disposable pulse oximeter assembly that includes a protective covering and a disposable pulse oximeter.

II. BACKGROUND OF THE INVENTION

With a few exceptions, tradition and technology have favored transillumination pulse oximetry in the operating theater. The principle of operation of the pulse oximeter sensor is fairly simple but is arguably the most important development in anesthesia monitoring in the twentieth century. Two wavelengths of light (usually 660 nm and 940 nm) are used to spectrophotometrically determine the ratio of oxidized to reduced hemoglobin noninvasively as well as to determine the pulsatility of blood plethysmographically. Presently, the most common application of this in the operating theater is via transillumination through the capillary bed of a peripheral digit. However, it is not unusual for multitrauma and thermally injured patients to either have severe peripheral vasoconstriction or to have severely damaged (or missing due to amputation) peripheral vascular beds. Reflectance oximetry rather than transillumination oximetry was the earliest investigative form of the technique. Transillumination pulse oximetry, without question, is the most effective form when oximetry is obtained through skin. However, when skin is not interposed as a barrier to capillary bed access, reflectance pulse oximetry easily can be achieved with very accurate results. The effect is achieved by the backscattering of incident bispectral light that traverses and, on reflection from nonabsorptive collagenous tissues, retraverses formed elements in the blood back to the oximetric detector. Rather than superseding transillumination pulse oximetry, this technique broadens the scope of possible monitoring sites, adding to the clinician's armamentarium.

Conventional pulse oximetry in the severely burned patient can be a significant challenge, yet these data are vital in operating room and intensive care settings. Most current oximetric approaches depend upon available peripheral sites permitting transillumination oximetry and indeed, this method is sufficient for most surgical conditions and procedures. Unfortunately, patients with severe burns often have few sites for the effective placement of the transilluminating pulse oximeter sensor. In addition, these patients often have severe circulatory compromise rendering the peripheral pulse oximeter less efficient. A variety of studies have shown that oral pulse oximeter sensors are more reliably and rapidly responsive than peripheral pulse oximeter sensors. However, many of these studies use oral transillumination pulse oximetry, held in place via complex devices or pieces of improvised malleable metal. Oral secretions, equipment failure, and placement difficulty often render these techniques ineffective.

Reflectance oximetry can be a useful tool where a capillary bed is easily accessible. Indeed, it is used commonly and effectively among intrapartum and neonatal patients whose capillary beds are easily accessed through their skin. The technique has also been applied to adult and pediatric burn patients by placing the reflectance sensor in wounds or over hyperemic sites such as healed partial thickness burns. There remain a variety of other useful capillary beds that will provide better and more accurate data and that are not easily attainable with current disposable pulse oximeter sensors.

Bodily fluids that come in contact with conventional, off-the-shelf disposable pulse oximeter sensors upon insertion into an open wound or body cavity negatively effect the operation of the pulse oximeter sensors. Disposable pulse oximeter sensors, like the Nellcor® Oxisensor® II D-25, will begin to electrically malfunction over time, because liquid from the body cavity or wound will begin to breakdown the protective material around the electrical components and then seep into the area around the electrical components and short circuit the disposable pulse oximeter sensor causing the sensor to malfunction.

It is difficult to predict when a disposable pulse oximeter sensor will malfunction due to exposure of its electrical components. Accordingly, a need exists for protecting off-the-shelf disposable pulse oximeter sensors with a disposable protective covering for use in areas with fluids.

III. SUMMARY OF THE INVENTION

This invention solves the ongoing problems of using off-the-shelf disposable pulse oximeter sensors in liquid filled cavities and/or wounds either in humans or animals. The invention, while addressing the problems of the prior art, obtains advantages that were not achievable with the prior art devices.

The invention encompasses a protective covering for protecting disposable off-the-shelf pulse oximeter sensor.

An object of the invention is to obtain oximetry measurements from more areas besides internal locations with either a complex or multipurpose apparatus or external locations.

Another object of the invention is to allow for lingual placement of a disposable pulse oximeter sensor for reflectance readings to provide efficient and clinically accurate pulse oximetry measurements.

Another object of the invention is to allow for buccal placement of a disposable pulse oximeter sensor for reflectance readings to provide efficient and clinically accurate pulse oximetry measurements.

An advantage of the invention is an improvement in the quality of care resulting from elimination of the need to set-up and assemble complex apparatuses to take internal oximetry measurements and readings.

Another advantage of the invention is improved pulse oximetry readings for disposable pulse oximeter sensors, because the pulse oximeter sensors will be protected from body fluids while maintaining the flexibility of the pulse oximeter sensors.

Another advantage of the invention is improved pulse oximetry readings for disposable pulse oximeter sensors, because when the invention is used internally within an individual or an animal, the skin will shield the pulse oximeter sensor from at least some lighting from the surrounding environment.

Another advantage of the invention is that a specialized probe and/or equipment are not required to take internal oximetry readings.

Another advantage of the invention is that reflectance pulse oximetry using the superior lingual surface and a standard disposable pulse oximeter sensor is a viable, efficient and cost effective way to monitor difficult to monitor patients during surgery.

Another advantage of the invention is that reflectance pulse oximetry using the buccal surface and a standard disposable pulse oximeter sensor is a viable, efficient and cost effective way to monitor difficult to monitor patients during surgery.

The invention accomplishes the above objectives and achieves the advantages. The invention is easily adapted to a wide variety of situations.

Given the following enabling description of the drawings, the apparatus should become evident to a person of ordinary skill in the art.

IV. BRIEF DESCRIPTION OF THE DRAWINGS

V. DETAILED DESCRIPTION OF THE INVENTION

Figure 1:
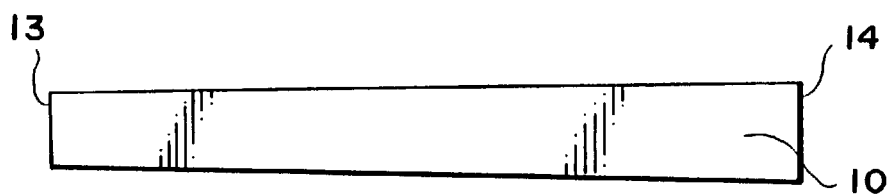
FIG. 1 illustrates a top view of a preferred embodiment.
Figure 2:
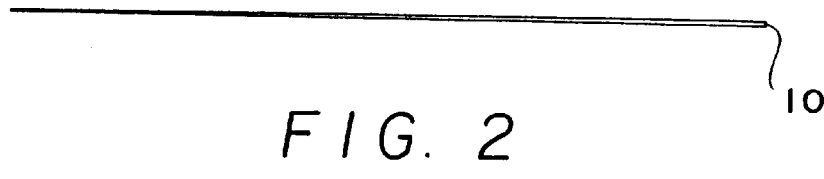
FIG. 2 illustrates a side view of the embodiment shown in FIG. 1.
Figure 5:
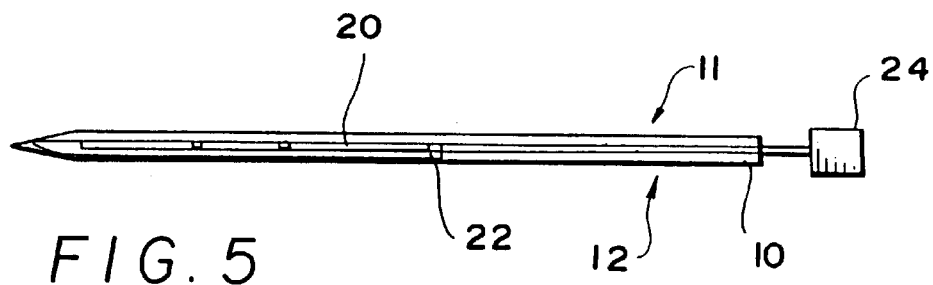
FIG. 5 illustrates a side view of the embodiment shown in FIG. 1 covering a disposable pulse oximeter sensor.
Figure 6:
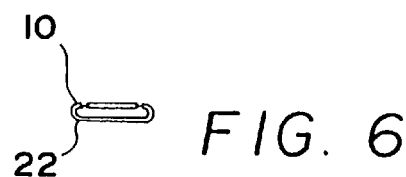
FIG. 6 illustrates an end view of the embodiment shown in FIG. 1 covering a disposable pulse oximeter sensor.

In accordance with the present invention, a combination pulse oximeter sensor assembly is provided including a pulse oximeter sensor and a protective covering. FIGS. 1 and 2 illustrate a preferred embodiment of the protective covering. FIGS. 5 and 6 depict the preferred embodiment of the combination disposable pulse oximeter sensor assembly. Like reference numerals in the figures represent and refer to the same element.

Figure 4:
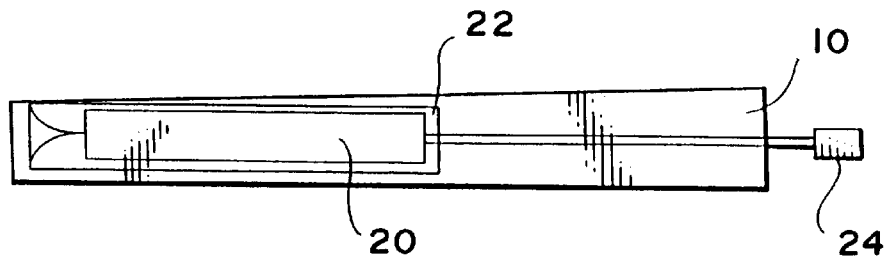
FIG. 4 illustrates a top view of the embodiment shown in FIG. 1 covering a disposable pulse oximeter sensor.

Referring to FIGS. 1 and 4, the protective covering 10 may include a condom, a shield or a protective sheath made from polypropylene, translucent rubber, or a similar material. Preferably the protective covering 10 includes a substantially transparent section to be disposed adjacent to a light source and a light detector of a pulse oximeter sensor 20 to facilitate light transmission to and from the pulse oximeter sensor 20. The protective covering 10 preferably includes a top surface 11 and a bottom surface 12. The protective covering 10 further includes a proximal end 14 and distal end 13 having a pocket formed therebetween. The distal end 13 preferably is sealed while the proximal end 14 includes an opening to allow insertion of the pulse oximeter sensor 20.

The pulse oximeter sensor 20 includes a light source, a light detector, wiring, probe fixing tape and/or plastic tape covers 22 and connector cable 24. The light source may be one or more light emitters such as light emitting diodes (LED), a bispectral emitter, a dual spectral emitter, a photoemitter, or a semiconductor die. The light detector may be one of the following: photoelectric receiver, photodetector, or a semiconductor die. The wiring includes conductive lines and contact electrodes.

In keeping with the invention, the pulse oximeter sensor 20 may be disposed within the protective covering 10. To facilitate insertion, removal and storage of the pulse oxime-ter sensor 20 in the protective covering 10, the proximal end 14 of the protective covering 10 preferably is wider than the distal end 13. In a preferred embodiment, the width of the pocket formed between the distal and proximal ends 13 and 14 increases along the length of the protective covering 10. In accordance with a particularly preferred feature of the invention, the change in width of the opening along the length of the protective covering 10 is approximately one-half centimeter.

Figure 3A:
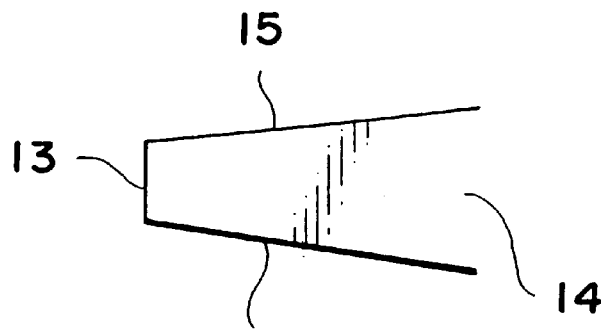
FIGS. 3a and 3b depict alternate embodiments of the protective covering in accordance with the invention.
Figure 3B:
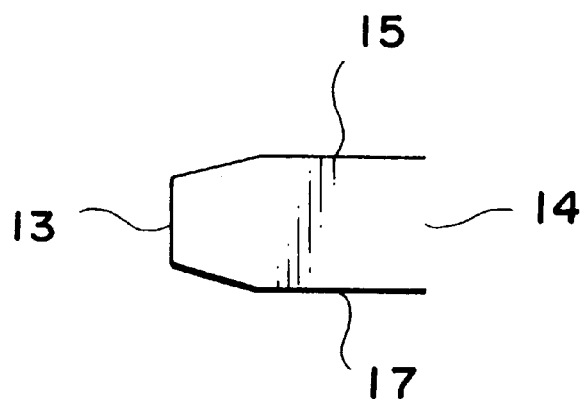

As one of ordinary skill in the art will realize, the protective covering 10 may be implemented in a variety of geometries. For example, in accordance with an aspect of the invention, the protective cover 10 may include first and second edges 15 and 17. In one embodiment, as shown in FIG. 1, the first edge 15 may be angularly displaced relative to the axis of the protective covering 10. In another embodiment, each of the first and second edges 15 and 17 may be angularly displaced from the axis of the protective covering as depicted in FIG. 3a. In still another embodiment, as illustrated in FIG. 3b, the first edge 15 may include a first section that is angularly displaced from the axis of protective covering 10 near the distal end 13 and a second section that is substantially parallel to the axis of protective covering 10 near the proximal end 14. The second edge 17 may be a mirror image of the first edge 15 or the second edge may be parallel to the axis of protective covering 10 along the entire length of protective covering 10 (not shown). One of ordinary skill in the art will appreciate that the forgoing constitutes only a representative sample of suitable geometries for the protective covering. Angularly displaced edges increase the convenience of using off-the-shelf pulse oximeter sensors, because the adhesive portions 22 can be folded inward without mutilating the pulse oximeter sensor by removing or excising the adhesive portions.

Furthermore, the protective covering 10 preferably is bilaminar in nature to contain a substantially rectangular pulse oximeter sensor 20 with probe fixing tape and/or plastic tape covers 22 folded back. The proximal end 14 may include a flap extending from either the top surface 11 or the bottom surface 12 to fold back and seal the protective covering 10 or some type of adhesive inside the pocket near the proximal end 14 to seal the protective covering 10. The protective covering 10 preferably covers and encases the pulse oximeter sensor 20 and a portion of the connector cable 24 extending from the pulse oximeter sensor 20.

In commercial applications, it is expected that the protective covering 10 will be disposable. The protective covering 10 may serve as an envelope like structure for the pulse oximeter sensor 20 to be inserted into for use. In particular, the structure of the protective covering 10 may be a blind flat bilaminar bag. As a result, the protective covering 10 insulates the pulse oximeter sensor 20 from direct contact with bodily or surgically related fluids, consequently, protecting the electrical components of the pulse oximeter sensor 20 from fluid.

The protective covering 10 is easily manufactured. In accordance with a preferred manufacturing method, the first step is to layout flat two sheets of polypropylene, or similar non-reactive material on a substantially flat surface such that the two sheets overlap in the area where the protective coverings will be formed. Then using a heat sealer or gun, the sheets may be subdivided into individual protective coverings. The heat sealer or gun will allow the manufacturer to subdivide the sheets' surface area into individual protective coverings that will have their sides formed by melting together the two sheets into seams. One of ordinary skill in the art will appreciate that the two sheets of polypropylene may be replaced with a large polypropylene, or similar material, bag. One of ordinary skill in the art will also appreciate that the two sheets of polypropylene may be replaced with one polypropylene, or similar material, sheet folded over such that the fold line forms the side of the protective coverings formed along the fold line.

The protective covering 10 will allow off-the-shelf disposable pulse oximeter sensors 20 to be used in a greater number of locations within patients or animals. In particular, oximetry will be able to be performed in the oral cavity on the lingual or buccal mucosa, the palate or the posterior pharynx, as well as on intravaginal or intrarectal capillary beds. However, the intrarectal capillary is not easy to take readings from because of the presence of feces and iron residue in the rectum. Also, pulse oximetry in any area where bodily or surgical fluids could otherwise cause contamination of the electrical parts of a pulse oximeter sensor 20. The protective covering 10 will also increase the possibilities of the disposal off-the-shelf pulse oximeter sensors 20 in veterinarian medicine. An example of a disposable pulse oximeter sensor 20 that will have increased use is the Nellcor® Oxysensor® II line of pulse oximeter probes and sensors (Nellcor Puritan Bennett®, Inc., Pleasanton, Calif.).

In connection with the lingual and buccal mucosas, reflectance pulse oximetry will be more easily performed without the use of complex and specialized probes. The insulation aspects of the protective covering 10 will allow for use of pulse oximeter sensors 20 for peribuccal, perilingual, sublingual, peripalatal, peripharyngeal, perivaginal, perirectal, and surgical site pulse oximetry. To take readings from the buccal surface, the patient's jaw should be opened to allow access to the buccal surface. The protective covering 10 with inserted pulse oximeter sensor 20 disposed therein may be placed against the buccal surface. As the jaw closes, the muscles will contract and close around the protective covering 10, thus holding the protective covering 10 and the pulse oximeter sensor 20 against the buccal surface. A much tighter fit is possible, because of the flexible nature of the combination of the protective covering 10 and the pulse oximeter sensor 20.

This assembly is able to perform lingual oximetry as described by the following discussion.

There is an often-overlooked capillary bed readily accessible in most adult burn patients that is as amenable to reflectance oximetry as the forehead of a premature infant. The tongue of a burned patient is seldom compromised no matter how severe the burn, and the capillary bed is close to the tongue surface. Transillumination pulse oximetry of the tongue has been documented as a viable method of monitoring, but not everyone has the equipment available to place a transilluminating pulse oximeter on the tongue. A reflectance pulse oximeter sensor has the light source and the light detector in a side-by-side configuration rather than in opposition. A disposable pulse oximeter probe such as the Nellcor® Oxisensor® II D-25 can easily be positioned this way. The device may be placed flat upon a suitable capillary bed and it thus becomes a reflectance pulse oximeter sensor. In this manner, a standard disposable finger pulse oximeter sensor may simply be placed flat on the tongue without any need for clamps or tape, thus rendering it a reflectance rather than a transilluminating device.

A method of taking pulse oximeter readings from the lingual and buccal surfaces within a patient has been submitted to actual testing in the below-described population and according to the following protocols.

In connection with studying pulse oximeter readings from the lingual surface, data was reviewed for eight difficult to monitor patients who were monitored via lingual reflectance pulse oximetry over 25 consecutive surgical procedures, all consisting of burn excision and grafting. Patients ranged in age from 26 to 57 years (Mean=36.0, Standard Deviation (SD)=10.3). Patients ranged from 20% to 92% total body surface area (% TBSA) burned (Mean=66.75%, SD=26.42). Number of operations per patient ranged from one to five (Mean=3.13, SD=1.55). Six of these eight patients arrived to the operating room intubated for all of the operations in this study. Two patients were induced and intubated in a standard fashion.

In each case, a Nellcor® Oxisensor® II D-25 was centered flat on the superior lingual surface with the detector and the bispectral emitter facing the lingual surface. This pulse oximeter orientation was used for the duration of each case. When clinically indicated, an arterial blood gas (ABG) sample was drawn and the $SpO_2$ (oxygen saturation of hemoglobin) noted for clinical monitoring and prior to transfusion in every case. All had multiple ABG's drawn and all patients were transfused. The ABG $SaO_2$ (oxygen saturation of arterial blood) was noted in each case.

Descriptive statistics and a concordance rate as well as a t-test for correlated means were calculated between the simultaneously obtained $SpO_2$ and $SaO_2$ values. The difference between the $SpO_2$ and $SaO_2$ values was insignificant by t-test for correlated means (t=1.25, df=24, NS). Upon inspection, the means were very close and the standard deviations were very small as were the SEM's, all suggesting very little difference or variability between these two measures of oxygen saturation. A concordance rate of 92% was calculated (+1.5%) showing a high degree of relationship between lingual and ABG $SaO_2$.

This data suggests that lingual reflectance oximetry is a simple, accurate means of monitoring arterial oxygen saturation in the severely burned patient where oximetric monitoring presents a challenge. An existing disposable pulse oximeter was utilized in this study saving the cost of specially designed equipment. Given that central oximetry has been shown to be more rapidly responsive to oxygen saturation variability than peripheral oximetry, there are few drawbacks and considerable benefit from this method. One drawback is that the technique is probably limited to intubated patients, as awake, extubated patients could find the presence of a lingual pulse oximeter irritating. However, this limitation would hold with lingual transillumination pulse oximetry as well. In addition to operating room considerations, ventilated patients in intensive care settings could benefit from this technique, especially given the more rapid response of a centrally placed pulse oximeter over a peripheral one.

In connection with studying pulse oximeter readings from the buccal surface, nine patients were monitored via buccal reflectance pulse oximetry over 20 consecutive surgical procedures, which procedures consisted of burn excision and grafting. Patients ranged in age from 23 to 56 years (Mean=34.8, SD=11.2) and ranged from 17% to 75% TBSA burned (Mean=44.3%, SD=28.9). Each patient received from one to eight operations (Mean=4.01). Five of these nine patients arrived to the operating room intubated for all of the operations in this study. Four patients were induced and intubated in a standard fashion for all surgical procedures.

A Nellcor® Oxisensor® II D-25 was placed intraorally between the lower teeth and the left or right buccal surface of the cheek and lip, with the bispectral emitter and sensor facing the buccal surface. This pulse oximeter configuration was used for the duration of each case. In addition, a similar disposable oximetric probe was placed on a peripheral digit in the commonly accepted transillumination configuration. At five minute intervals throughout the case, values for both oximetric probes were coded on the anesthesia record.

The differences between the peripheral and buccal $SpO_2$ values were insignificant by t-tests for correlated means. Concordance rates as percent agreements were calculated for all cases. Average percent agreement was 84% ranging from 25% to 100%. Three of the 20 samples had percent agreements less than 91%. In each of these case, the peripheral pulse oximeter appears to have failed, in two cases secondary to sepsis, and in another secondary to peripheral vasoconstriction in the face of a norepinepherine infusion. Buccal $SpO_2$ readings in all three cases continued to be 97% or greater.

This data suggests that buccal reflectance oximetry is a simple, accurate means of monitoring arterial oxygen saturation in the severely burned patient where oximetric monitoring presents a challenge. Given that central oximetry has been shown in numerous studies to be more rapidly responsive to oxygen saturation variability than peripheral oximetry, as well as more directly reflective of central oxygen saturation, there are few drawbacks and considerable benefit from this method. Indeed, in the three examples in this study where percent agreements were low, the peripheral oximetric probes were returning apparently erratic and/or generally low values while buccal oximetric readings remained at 97% or higher. All three of these patients had peripheral vascular compromise secondary to sepsis and/or a vasoconstricting agent (norepinepherine infusion).

It may appear from the study results, at first blush, that a full range of $SpO_2$ values was not tested and that the continuously high $SpO_2$ readings are spurious to the technique. On the contrary, in order to obtain a $SpO_2$ value greater or less than 85% a very specific set of relationships must be present relative to the bispectral emitter and light sensing oximetric elements. Thus, spuriously high values in particular do not consistently occur. High $SpO_2$ values require the presence of saturated hemoglobin. Unlike lingual oximetry, this technique is not necessarily limited to intubated patients as a flat disposable oximetric probe could be placed between the cheek and teeth of an awake patient. In addition to operating room considerations, ventilated patients in intensive care settings could benefit from this technique, especially given the more rapid response of a centrally placed pulse oximeter over a peripheral one.

Those skilled in the art will appreciate that various adaptations and modifications of the above-described preferred embodiments can be configured without departing from the scope and spirit of the invention. Therefore, it is to be understood that, within the scope of the appended claims, the invention may be practiced and constructed other than as specifically described herein.

What is claimed is:

1. In combination:
   a protective covering having a bottom surface, a top surface, a sealed distal end and an open proximal end cooperating to form a pocket, wherein one of the bottom and top surfaces includes a substantially translucent section;
   a pulse oximeter having a light source and a light detector, said pulse oximeter being deployable in the pocket such that the substantially transparent section is positioned adjacent the light source and the light detector; and
   wherein the bottom surface and the top surface are joined along first and second seal edges and at least a section of one of said first edge and said second edge is divergent from at least a section of the other of said first edge and said second edge.

2. The combination according to claim 1, wherein the bottom surface and the top surface are integrally formed.

3. The combination according to claim 2, wherein said protective cover is made of polypropylene.

4. The combination according to claim 1, wherein said protective covering is made of polypropylene.

5. The combination according to claim 1, wherein said protective covering is multilaminar.

6. The combination according to claim 1, wherein the first edge is substantially parallel to a longitudinal axis of said protective covering and the second edge is angularly displaced with respect to the longitudinal axis of said protective covering.

7. The combination according to claim 1, wherein the first and second edges are angularly displaced from the longitudinal axis of said protective covering.

8. The combination according to claim 7, wherein the angular displacement of the first edge is greater than the angular displacement of the second edge.

9. The combination according to claim 1, wherein the first and second edges are angularly displaced from the longitudinal axis of said protective covering.

10. The combination according to claim 1, wherein one of the top and bottom surfaces includes a flap extending such that said flap is capable of being folded over the open proximal end to form a seal.

11. A method of monitoring arterial oxygen saturation comprising:
    contacting a patient's lingual surface with the combination according to claim 1, and;
    maintaining the combination of claim 1 in contact with the lingual surface for a measurement period.

12. A method of monitoring arterial oxygen saturation comprising:
    contacting a patient's buccal surface with the combination according to claim 1, and;
    maintaining the combination of claim 1 in contact with the buccal surface for a measurement period.

13. A protective covering for a pulse oximeter sensor comprising:
    a bottom surface,
    a top surface joined to the bottom surface along first and second sealed edges,
    a sealed distal end, and
    an open proximal end, wherein
    said top and bottom surfaces and said proximal and distal ends cooperate to form a pocket for receiving the pulse oximeter sensor,
    at least one of the bottom and top surfaces including a substantially translucent section, and
    at least the first seal edge is angularly displaced in a widthwise direction from a longitudinal axis of the pocket.

14. The protective covering according to claim 13, wherein said bottom surface and said top surface are made of polypropylene.

15. The protective covering according to claim 13, wherein one of the bottom surface and the top surface includes a flap extending such that said flap is capable of being folded over the open proximal end.

16. The protective covering according to claim 13, wherein the second seal edge is angularly displaced from the longitudinal axis of the pocket.

17. The protective covering according to claim 13, wherein the second seal edge is substantially parallel to the longitudinal axis of the pocket.

18. The protective covering according to claim 13, wherein each of the first and second seal edges include a section that is angularly displaced from the longitudinal axis of the pocket and a section that is substantially parallel to the longitudinal axis of the pocket.

19. The protective covering according to claim 13, wherein the sealed distal end is narrower than the open proximal end.

* * * * *